United States Patent
Hyon et al.

(10) Patent No.: US 8,620,219 B2
(45) Date of Patent: Dec. 31, 2013

(54) WIRELESS COMMUNICATION SYSTEM BETWEEN MEDICAL DEVICES USING COGNITIVE TECHNOLOGY

(75) Inventors: Tae In Hyon, Hwaseong-si (KR); Sung Jin Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 291 days.

(21) Appl. No.: 13/157,554

(22) Filed: Jun. 10, 2011

(65) Prior Publication Data
US 2012/0172075 A1 Jul. 5, 2012

(30) Foreign Application Priority Data
Dec. 30, 2010 (KR) .......................... 10-2010-0138489

(51) Int. Cl.
H04B 15/00 (2006.01)

(52) U.S. Cl.
USPC ......... 455/62; 455/63.1; 455/67.13; 455/501; 455/509; 455/512; 455/307; 375/275; 375/367; 375/346

(58) Field of Classification Search
USPC .................. 455/62, 63.1, 501, 509, 512, 307, 455/67.13; 375/367, 275; 340/539.1; 342/94; 333/12; 327/552
See application file for complete search history.

(56) References Cited

U.S. PATENT DOCUMENTS

| | | | | |
|---|---|---|---|---|
| 7,130,396 B2* | 10/2006 | Rogers et al. | ............ | 379/106.02 |
| 7,917,110 B2* | 3/2011 | Horiguchi et al. | ......... | 455/164.1 |
| 8,121,630 B2* | 2/2012 | Kwon et al. | .................. | 455/522 |
| 8,155,649 B2* | 4/2012 | McHenry et al. | ............. | 455/434 |
| 8,165,235 B2* | 4/2012 | Teng et al. | ..................... | 375/260 |
| 8,175,539 B2* | 5/2012 | Diener et al. | ................... | 455/69 |
| 8,184,656 B2* | 5/2012 | Chandra et al. | ............... | 370/445 |
| 8,208,391 B2* | 6/2012 | Gurney et al. | ................ | 370/252 |
| 8,301,081 B2* | 10/2012 | Aboba et al. | ................. | 455/41.2 |
| 8,326,313 B2* | 12/2012 | McHenry et al. | ............. | 455/454 |
| 8,340,071 B2* | 12/2012 | Sadri et al. | ..................... | 370/344 |
| 8,391,794 B2* | 3/2013 | Sawai et al. | ..................... | 455/62 |
| 8,412,247 B2* | 4/2013 | Junell et al. | ................... | 455/509 |
| 2004/0146149 A1 | 7/2004 | Rogers et al. | | |
| 2006/0239367 A1* | 10/2006 | Wilhelmsson et al. | ....... | 375/260 |
| 2008/0194925 A1 | 8/2008 | Alsafadi et al. | | |
| 2009/0086837 A1* | 4/2009 | Teng et al. | ..................... | 375/260 |
| 2010/0046583 A1 | 2/2010 | So et al. | | |
| 2010/0069013 A1 | 3/2010 | Chaudhri et al. | | |

(Continued)

FOREIGN PATENT DOCUMENTS

| KR | 10-2003-0031007 | 4/2003 |
|---|---|---|
| KR | 10-2007-0096493 | 10/2007 |

(Continued)

Primary Examiner — Marceau Milord
(74) Attorney, Agent, or Firm — NSIP Law

(57) ABSTRACT

Provided is a wireless communication system between medical devices. A wireless communication apparatus between medical devices using a cognitive technology may receive, from an external frequency coordination database server, state information of frequencies that are available in a predetermined area, and store interference information associated with the frequencies. The communication apparatus may sense an external interference signal that affects the frequencies outside the predetermined area, and an internal interference signal that affects the frequencies within the predetermined area. The communication apparatus may determine a priority of each of the frequencies that are available in the predetermined area based on the interference information, the external interference signal, and the internal interference signal, and may determine a frequency to be assigned based on the priority.

27 Claims, 10 Drawing Sheets

(56) References Cited

U.S. PATENT DOCUMENTS

2010/0105332 A1* 4/2010 McHenry et al. ............... 455/62
2010/0135238 A1 6/2010 Sadri et al.
2010/0195590 A1 8/2010 Park
2012/0294168 A1* 11/2012 Freda et al. .................. 370/252

FOREIGN PATENT DOCUMENTS

| KR | 10-2009-0025123 | 3/2009 |
| KR | 10-2009-0026661 | 3/2009 |
| KR | 10-2009-0089036 | 8/2009 |

* cited by examiner

FIG. 5B

*Available frequency ☐

| Time | t1 | t2 | t3 | t4 | t5 | t6 | t7 | t8 | t9 |
|------|----|----|----|----|----|----|----|----|----|
| Rank 1 | F1 | F2 | F2 | F2 | F2 | F3 | F3 | F3 | F3 |
| Rank 2 | F2 | F3 | F3 | F3 | F3 | F5 | F5 | F5 | F5 |
| Rank 3 | F3 | F4 | F5 | F1 | F1 | F1 | F1 | F1 | F1 |
| Rank 4 | F4 | F5 | F4 | F5 | F5 | F2 | F2 | F2 | F2 |
| Rank 5 | F5 | F1 | F1 | F4 | F4 | F4 | F4 | F4 | F4 |

WIRELESS COMMUNICATION SYSTEM BETWEEN MEDICAL DEVICES USING COGNITIVE TECHNOLOGY

CROSS-REFERENCE TO RELATED APPLICATION(S)

This application claims the benefit under 35 U.S.C. §119(a) of Korean Patent Application No. 10-2010-0138489, filed on Dec. 30, 2010, in the Korean Intellectual Property Office, the entire disclosure of which is incorporated herein by reference for all purposes.

BACKGROUND

1. Field

The following description relates to a wireless communication system between medical devices, and more particularly, to a system for controlling internal channel interference and external channel interference with respect to a frequency that is used between medical devices.

2. Description of Related Art

Often, a frequency that is used for a medical use between medical devices may not be designated exclusively for the medical use. For example, a band of 402 MHz to 405 MHz may be permitted for medical use as a secondary service, but must yield to the weather and scientific satellite primary service. Accordingly, channel interference may occur on that frequency band. Even in a frequency band, for example, of 608 MHz to 614 MHz, which is allowed for medical use as a primary service, channel interference may occur.

The reliability may be most important in communication between medical devices. Accordingly, if a slightest difference exists, it may become a significant issue to secure the reliability of measured medical information. In general, interference may occur on an internal channel and an external channel and may obstruct the reliability of the medical equipment.

SUMMARY

In one general aspect, there is provided a wireless communication apparatus between medical devices using a cognitive technology, the apparatus including a frequency database management unit to receive, from an external frequency coordination database server, state information of frequencies that are available in a predetermined area, and to store interference information that is associated with the frequencies, an interference signal sensing unit to sense an external interference signal that affects the frequencies outside the predetermined area, and an internal interference signal that affects the frequencies within the predetermined area, and a control unit to determine a priority of each of the frequencies that are available in the predetermined area based on the interference information, the external interference signal, and the internal interference signal, and to determine a frequency to be assigned based on the priority.

The external frequency coordination database server may be configured to store information about whether the frequencies are used by a predetermined device that is outside and within the predetermined area.

The interference signal sensing unit may comprise an external interference signal sensing unit to sense the external interference signal, and an internal interference signal receiver to receive, from a mobile hub, the internal interference signal and positioning information of a wireless node that is positioned within the predetermined area.

The control unit may be configured to determine the priority of each of the frequencies that are available in the predetermined area based on an amount of interference that is measured during a predetermined amount of time.

The control unit may be configured to determine the priority of each of the frequencies that are available in the predetermined area based on a duration of interference that affects each of the frequencies at a predetermined point in time with respect to each of the frequencies, an amount of power of the interference, and a last point in time at which the interference occurs before the predetermined point in time.

The control unit may be configured to determine the frequency to be assigned based on a quality of service (QoS) of a wireless node.

The interference signal sensing unit may be configured to sense interference of a heterogeneous protocol that affects a frequency assigned to a mobile hub, and the control unit may be configured to assign an alternative frequency to the mobile hub in response to the interference of the heterogeneous protocol being sensed.

In another aspect, there is provided a wireless communication apparatus between medical devices using a cognitive technology, the apparatus including an interference signal sensing unit to sense an internal interference signal that affects frequencies that are available in a predetermined area, a receiver to receive assigned frequencies from a local channel coordinator, and to receive sensing information from at least one sensor node, a transmitter to transmit the sensed internal interference signal to the local channel coordinator, and a control unit to determine a frequency to be reassigned to the at least one sensor node among the assigned frequencies based on the internal interference signal.

The interference signal sensing unit may be configured to sense an internal interference signal that affects the assigned frequencies, and to sense position information of a mobile hub and position information of at least one sensor node.

The transmitter may be configured to transmit the internal interference signal that affects the assigned frequencies, the position information of the mobile hub, and the position information of the at least one sensor node.

The control unit may be configured to determine frequencies to be reassigned to wireless nodes from among the assigned frequencies based on a QoS of each of the wireless nodes, and the wireless nodes may comprise the at least one sensor node and a medical measurement device.

The control unit may be configured to reassign, to the wireless nodes, frequencies that have relatively high priorities from among the assigned frequencies to wireless nodes that have a higher QoS ranking.

The interference signal sensing unit may be configured to sense interference of a heterogeneous protocol that affects the assigned frequencies, and the control unit may be configured to generate a signal for requesting the local channel coordinator for an alternative frequency in response to the interference of the heterogeneous protocol being sensed.

The transmitter may be configured to transmit, to the local channel coordinator, a signal for requesting assignment of a frequency and the signal for requesting the alternative frequency.

The apparatus may further comprise a buffer to store sensing information from the at least one sensor node.

In another aspect, there is provided a wireless communication network system between medical devices using a cognitive technology, the system including a local channel coordinator to determine a priority of each of the frequencies that are available in a predetermined area based on state information of frequencies that is received from an external frequency coordination database server, an external interference signal, and an internal interference signal, and to assign frequencies based on the priority, a mobile hub to sense the internal interference signal, to transmit the internal interference signal, to receive the assigned frequencies, and to reassign the assigned frequencies to a plurality of wireless nodes, and the plurality of wireless nodes to perform communication based on the reassigned frequencies.

The plurality of wireless nodes may comprise at least one sensor node or at least one medical measurement device, and each sensor node may comprise a first receiver to receive a first frequency that is reassigned from the mobile hub, a biosignal sensing unit to sense a biosignal, and a transmitter to transmit the biosignal to the mobile hub, and each medical measurement device may comprise a second receiver to receive a second frequency that is reassigned from the mobile hub and the biosignal.

The mobile hub may be configured to assign a frequency that has a relatively high priority from among the assigned frequencies to the at least one sensor node over the at least one medical measurement device.

In another aspect, there is provided a wireless communication method between medical devices using a cognitive technology, the method including receiving, from an external frequency coordination database server, state information of frequencies that are available in a predetermined area, and storing interference information associated with the frequencies, sensing an external interference signal that affects the frequencies outside the predetermined area, and an internal interference signal that affects the frequencies within the predetermined area, determining a priority of each of the frequencies that are available in the predetermined area based on the interference information, the external interference signal, and the internal interference signal, and assigning a frequency based on the priority.

The sensing may comprise receiving, from a mobile hub, the internal interference signal and positioning information of a wireless node that is positioned within the predetermined area.

The determining of the priority may comprise determining the priority of each of the frequencies that are available in the predetermined area based on an amount of interference that is measured during a predetermined amount of time.

The sensing may comprise sensing interference of a heterogeneous protocol that affects a frequency assigned to a mobile hub, and the assigning may comprise assigning an alternative frequency to the mobile hub in response to the interference of the heterogeneous protocol being sensed.

In another aspect, there is provided a wireless communication method between medical devices using a cognitive technology, the method including sensing an internal interference signal that affects frequencies that are available in a predetermined area, receiving assigned frequencies from a local channel coordinator, and receiving sensing information from at least one sensor node, transmitting the sensed internal interference signal to the local channel coordinator, and reassigning one of the assigned frequencies to the at least one sensor node based on the internal interference signal.

The sensing may comprise sensing an internal interference signal that affects the assigned frequencies, and sensing position information of a mobile hub and position information of at least one sensor node.

The transmitting may comprise transmitting the internal interference signal that affects the assigned frequencies, the position information of the mobile hub, and the position information of the at least one sensor node.

The reassigning may comprise reassigning, to the wireless nodes, frequencies that have relatively high priorities from among the assigned frequencies to wireless nodes that have a higher QoS ranking.

The sensing may comprise sensing interference of a heterogeneous protocol that affects the assigned frequencies, and requesting the local channel coordinator for an alternative frequency in response to the interference of the heterogeneous protocol being sensed.

Other features and aspects may be apparent from the following detailed description, the drawings, and the claims.

BRIEF DESCRIPTION OF THE DRAWINGS

FIG. 5A and FIG. 5B are diagrams illustrating examples of a wireless communication apparatus between medical devices that determines a priority of an available frequency in a cognitive radio environment.

Figure 1:
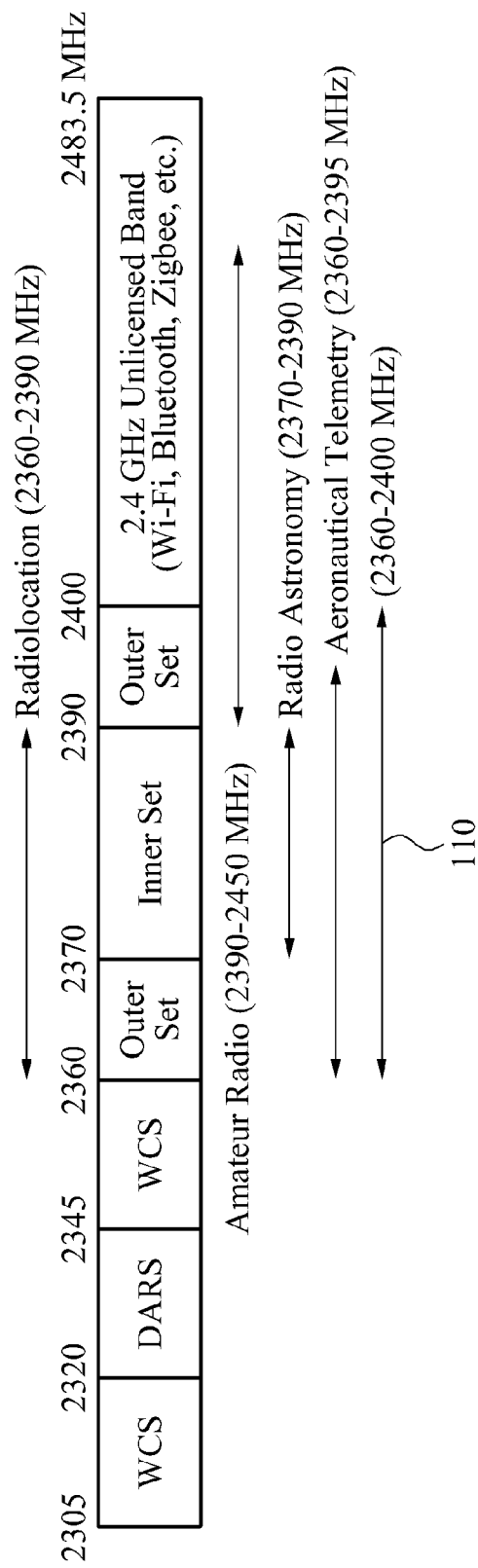
FIG. 1 is a diagram illustrating an example of a frequency band to be used for a medical use.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. Also, description of well-known functions and constructions may be omitted for increased clarity and conciseness.

FIG. 1 illustrates an example of a frequency band to be used for a medical use.

Referring to FIG. 1, an interval 110 corresponds to a frequency band from 2360 MHz to 2400 MHz. The interval 110 may be used as a frequency band for a medical use, for example, a medical body area network.

Referring to FIG. 1, the frequency band of 2360 MHz to 2400 MHz overlaps with each of a radiolocation frequency band of 2360 MHz to 2390 MHz, an amateur radio frequency band of 2390 MHz to 2450 MHz, a radio astronomy frequency band of 2370 MHz to 2390 MHz, and an aeronautical telemetry frequency band of 2360 MHz to 2395 MHz.

Even though the frequency band of 2360 MHz to 2400 MHz is used as the frequency band for the medical use, interference may occur due to the other overlapping frequency bands of other protocols.

Described herein is an apparatus and method that may hierarchically manage an available frequency band to reduce interference between a medical frequency band and a frequency band of another protocol.

Figure 2:
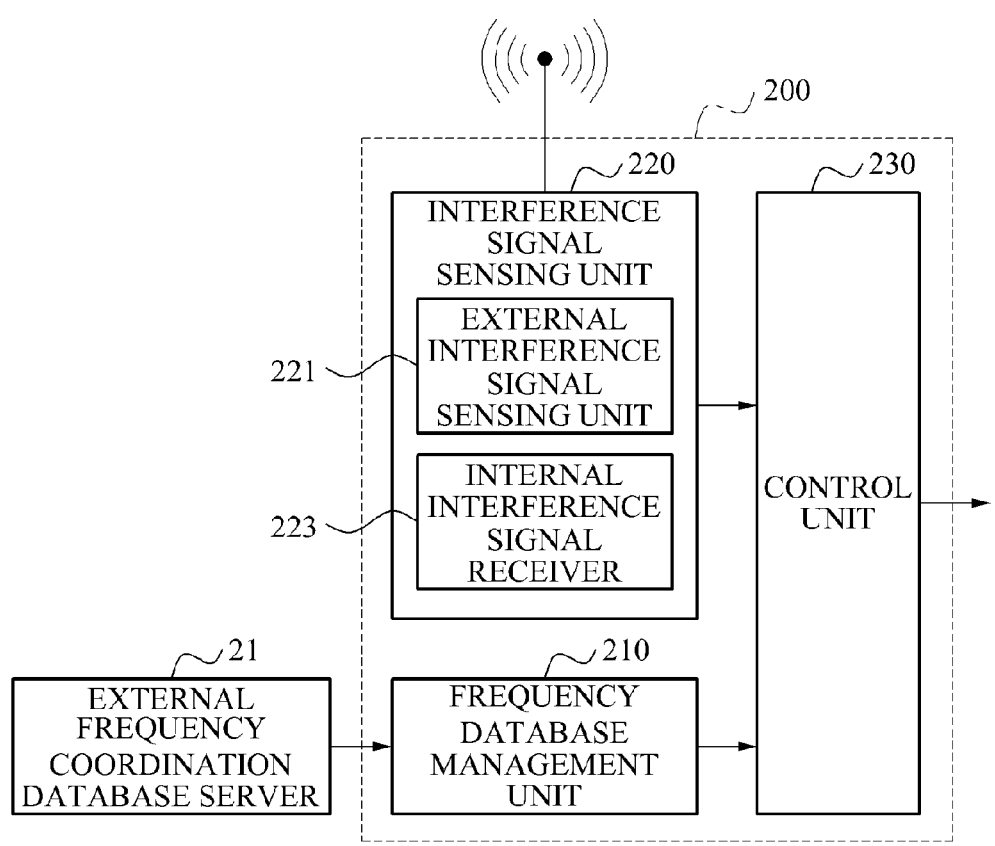
FIG. 2 is a diagram illustrating an example of a wireless communication apparatus between medical devices using a cognitive technology.

FIG. 2 illustrates an example of a wireless communication apparatus between medical devices using a cognitive technology.

Referring to FIG. 2, wireless communication apparatus 200 includes a frequency database management unit 210, an interference signal sensing unit 220, and a control unit 230.

The frequency database management unit 210 may receive, from an external frequency coordination database server 21, state information of frequencies that are available in a predetermined area, and may store interference information associated with the available frequencies. The state information may indicate whether the available frequencies are being used for a use other than a medical use. For example, the state information may include information about which band in the frequency band of 2360 MHz to 2400 MHz is being used for an amateur radio, an aeronautical telemetry, and the like.

The predetermined area may indicate an area in which a frequency being used by a medical device may be controlled using the wireless communication apparatus 200. The frequency database management unit 210 may update the state information periodically or at predetermined time intervals. The frequency database management unit 210 may store interference information that is associated with the available frequencies based on the state information.

The external frequency coordination database server 21 may store information about whether the available frequencies are used by a predetermined device outside and within the predetermined area. The predetermined device may include a medical device or a device being used for another use other than a medical use.

Frequency use information may be pre-registered to the external frequency coordination database server 21 for each use, for each position, and for each time.

The interference signal sensing unit 220 may sense an external interference signal that affects the available frequencies outside the predetermined area, and an internal interference signal that affects the available frequencies within the predetermined area. The available frequencies may correspond to frequencies assignable to a medical device and a sensor node performing low power communication.

The interference signal sensing unit 220 may sense the external interference signal and the internal interference signal periodically or at predetermined time intervals.

Interference may occur in the available frequencies due to a device that is not registered with the external frequency coordination database server 21. The external interference signal may indicate an interference signal occurring outside the predetermined area, and the internal interference signal may indicate an interference signal occurring within the predetermined area.

The interference signal sensing unit 220 may include an external interference signal sensing unit 221 and an internal interference signal receiver 223.

For example, when the predetermined area may be a hospital and a portion of available frequencies may be used for the medical use or for another use outside the hospital. A portion of available frequencies may be used for the medical use or for another use within the hospital.

The interference signal sensing unit 220 may sense frequencies that are being used by the other devices among the available frequencies.

The external interference signal sensing unit 221 may sense the external interference signal. For example, if the predetermined area is a hospital, the external interference signal sensing unit 221 may sense the external interference signal occurring outside the hospital.

The internal interference signal receiver 223 may receive the internal interference signal and positioning information of a wireless node that is positioned within the predetermined area. For example, the interference signal receiver 223 may receive the interference signal from a mobile hub. For example, if the predetermined area is a hospital, the internal interference signal receiver 223 may sense the internal interference signal occurring within the hospital.

A sensing coverage of the internal interference signal receiver 223 may be small, and the internal interference signal receiver 223 may receive the internal interference signal sensed at the mobile hub from a mobile hub positioned within the hospital.

For example, the mobile hub may perform a low data rate (LDR) low power communication with a wireless node, and may perform a high data rate (HDR) high spectral efficient (HSE) communication with the internal interference signal receiver 223. The mobile hub may include a communication terminal.

The control unit 230 may determine a priority of each of the frequencies that are available in the predetermined area. For example, the control unit may determine the priority based on the interference information stored in the frequency database management unit 210, the external interference signal sensed by the external interference signal sensing unit 221, and the internal interference signal sensed by the internal interference signal sensing unit 223. The control unit 230 may generate a ranking list based on the priority of each of the available frequencies.

The control unit 230 may determine a frequency to be assigned based on the priority. For example, the control unit 230 may assign a frequency to the mobile hub based on the priority. The mobile hub may reassign the assigned frequency to the wireless node. The wireless node may include a sensor node that is attached to a human body to sense a biosignal and a medical measurement device to analyze the biosignal.

The medical device may include the mobile hub and the wireless node.

The control unit 230 may determine the priority of each of the frequencies that are available in the predetermined area based on an amount of interference that is measured during a predetermined amount of time. The control unit 230 may determine frequencies that have an amount of interference less than or equal to a reference value as the frequencies to be assigned.

The control unit 230 may determine the priority of each of the frequencies that are available in the predetermined area by employing, as factors, a duration of interference affecting each of the frequencies at a predetermined point in time, an amount of power of interference, and a last point in time at which the interference occurs before the predetermined point in time.

The control unit 230 may determine the priority of each of the available frequencies by assigning a different weight to each of the factors. Examples of assigning weights to the factors is further described with reference to FIG. 4, FIG. 5A, and FIG. 5B.

The control unit 230 may determine a frequency to be assigned based on a quality of service (QoS) of the wireless node. Each wireless node may have a different QoS. The control unit 230 may determine the frequency to be assigned so that a frequency having a higher priority may be assigned to a wireless node having a higher ranking QoS.

The interference signal sensing unit 220 may sense interference of a heterogeneous protocol that affects the frequency that is assigned to the mobile hub. In response to sensing the interference of the heterogeneous protocol, the control unit 230 may assign an alternative frequency to the mobile hub.

For example, if the frequency is assigned to the mobile hub, the interference signal sensing unit 220 may sense frequency interference to the frequency of another use other than a medical use. In this example, the control unit 230 may replace the frequency currently assigned to the mobile hub with an alternative frequency that has a high priority.

Figure 3:
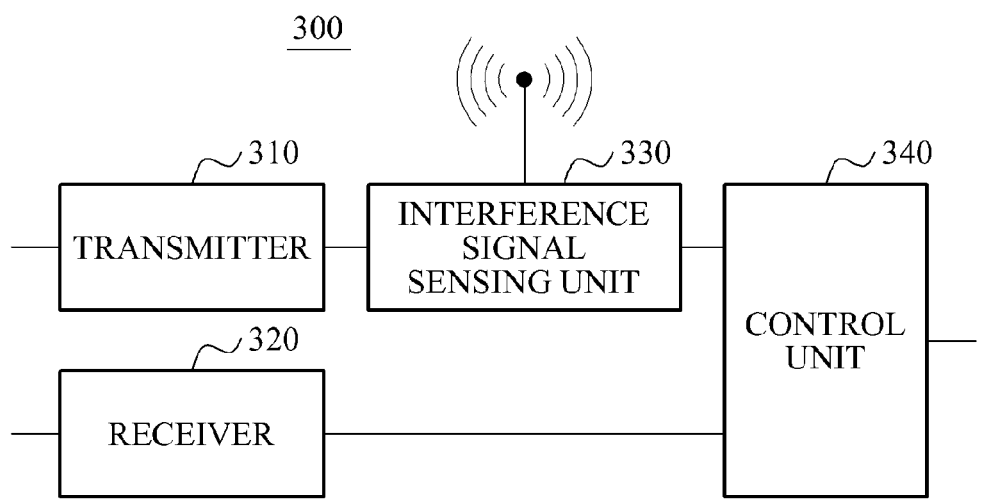
FIG. 3 is a diagram illustrating another example of a wireless communication apparatus between medical devices using a cognitive technology.

FIG. 3 illustrates another example of a wireless communication apparatus between medical devices using a cognitive technology.

The wireless communication apparatus 300 includes a transmitter 310, a receiver 320, an interference signal sensing unit 330, and a control unit 340.

The transmitter 310 may transmit a sensed internal interference signal to a local channel coordinator. The local channel coordinator is an example of the wireless communication apparatus 200 of FIG. 2. The wireless communication apparatus 300 of FIG. 3 is an example of a mobile hub.

The internal interference signal may indicate an interference signal that affects a frequency assigned to the mobile hub within a predetermined area.

The transmitter 310 may transmit the internal interference signal and position information to the local channel coordinator. For example, the position information may include position information of the mobile hub and the at least one sensor node. The local channel coordinator may assign an available frequency to the mobile hub based on the received position information. It should also be appreciated that a plurality of mobile hubs may be present.

The transmitter 310 may transmit a signal for requesting assignment of a frequency and a signal for requesting an alternative frequency, to the local channel coordinator. To assign a frequency used for communication with the wireless node, the transmitter 310 may transmit the signal for requesting the assignment of the available frequency, to the local channel coordinator.

In this example, the alternative frequency is a frequency that is replaceable if interference of another use or another medical device occurs on the frequency assigned to the mobile hub. The transmitter 310 may transmit the signal for requesting the assignment of the alternative frequency to the local channel coordinator in order to perform stable communication with the wireless node.

The receiver 320 may receive assigned frequencies from the local channel coordinator, and may receive sensing information from at least one sensor node. The receiver 320 may receive a biosignal from a sensor node that is attached to a human body to sense the biosignal.

The interference signal sensing unit 330 may sense an internal interference signal that affects frequencies available in a predetermined area, within the predetermined area. The interference signal sensing unit 330 may sense the internal interference signal that affects frequencies available for the medical use. The interference signal sensing unit 330 may sense the internal interference signal that affects the frequency assigned from the local channel coordinator. The interference signal sensing unit 330 may sense position information of a mobile hub and position information of at least one sensor node.

The control unit 340 may determine a frequency to be reassigned to at least one sensor node from among frequencies that are assigned from the local channel coordinator, based on the internal interference signal. If a sensor node is attached to or included in a human body, the control unit 340 may reassign a frequency that has a relatively high priority among the assigned frequencies.

The control unit 340 may determine frequencies to be reassigned to wireless nodes based on a QoS of each of the wireless nodes. The wireless nodes may include the sensor node and a medical measurement device.

The control unit 340 may reassign, to the wireless nodes, assigned frequencies having a higher priority to wireless nodes that have a higher ranking QoS. As described herein, the wireless nodes may include the sensor node and the medical measurement device. Because the control unit 340 reassigns an assigned frequency having a relatively high priority to a wireless node having a relatively high ranking QoS, it is possible to guarantee the reliability of a communication.

The interference single sensing unit 330 may sense interference of a heterogeneous protocol that affects the assigned frequencies. The control unit 340 may generate a signal for requesting the local channel coordinator for an alternative frequency, in response to the interference of the heterogeneous protocol being sensed.

The interference signal sensing unit 330 may sense interference that affects frequencies assigned to the mobile hub. The control unit 340 may generate a signal for requesting the local channel coordinator for an alternative frequency that may replace a currently assigned frequency.

A ranking list of currently available frequencies that is determined based on priorities may be stored in the local channel coordinator. Accordingly, a higher ranking frequency excluding the frequency assigned to the mobile hub may be determined as an alternative frequency.

In various aspects, the wireless communication apparatus 300 may include a buffer (not shown). The buffer may store information that is sensed by at least one sensor node. The sensing information may be stored in the buffer and may be stably transferred to another device.

Figure 4:
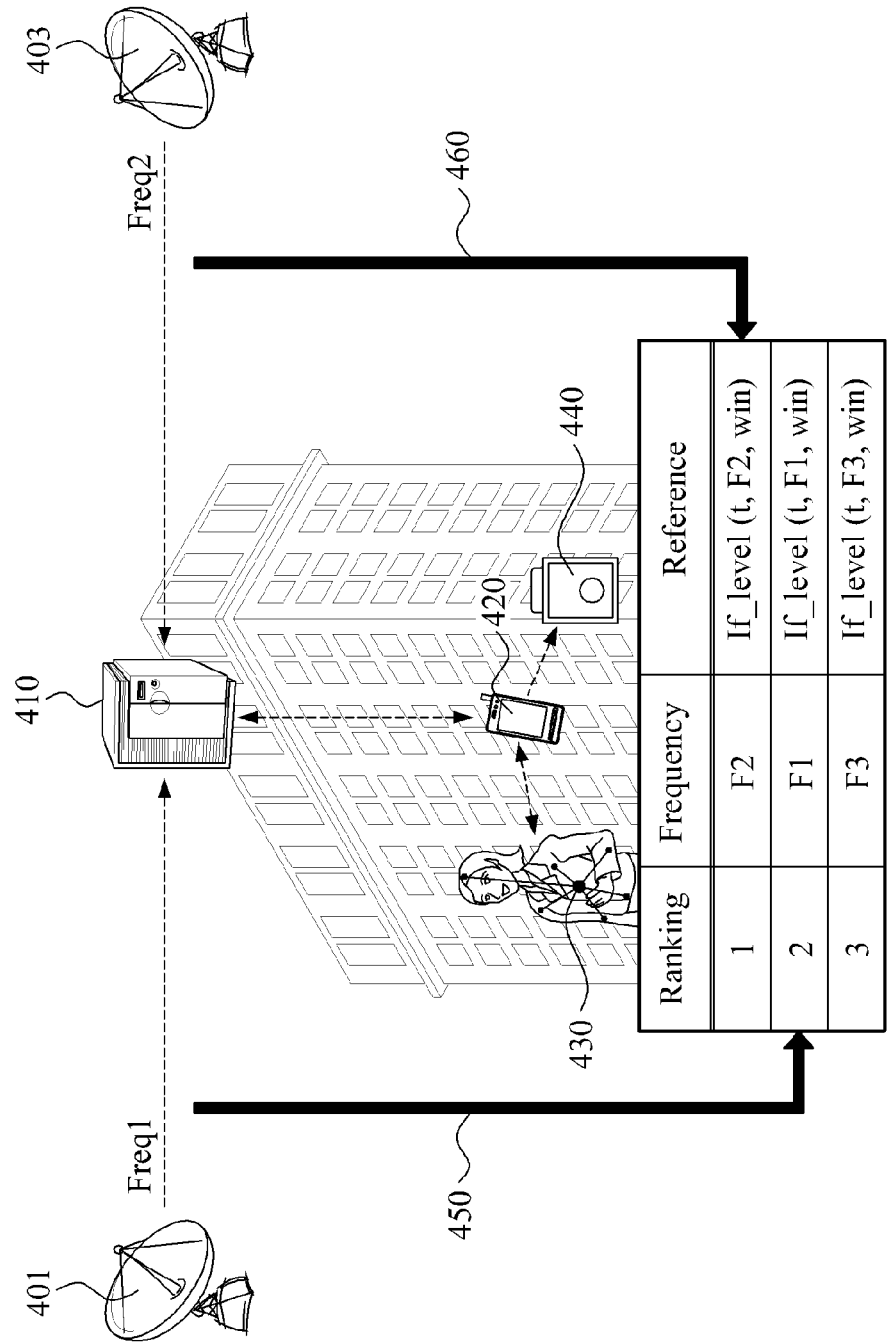
FIG. 4 is a diagram illustrating an example of an operation of a control unit that is included in a wireless communication apparatus between medical devices using a cognitive technology.

FIG. 4 illustrates an example of an operation of a control unit that is included in a wireless communication apparatus between medical devices using a cognitive technology.

Referring to FIG. 4, the wireless communication apparatus is an example of a local channel coordinator 410. The local channel coordinator 410 may obtain information associated with a frequency being used among available frequencies. For example, the local channel coordinator 410 may obtain the information from an external frequency coordination database server.

The local channel coordinator 410 may obtain interference information that affects the available frequencies by sensing an external interference signal and by receiving an internal interference signal from a mobile hub 420. A first frequency 401 and a second frequency 403 may correspond to frequencies for another use among the available frequencies. For example, the first frequency 401 and the second frequency 403 may correspond to interference signals.

A control unit of the local channel coordinator 410 may determine a ranking for the frequencies available for the medical use, based on an interference signal. The control unit may assign, to the mobile hub 420, frequencies that have relatively high rankings at a predetermined point in time. The mobile hub 420 may reassign the assigned frequencies to a sensor node 430 and a medical measurement device 440.

A ranking of a predetermined frequency may be determined based on a time and a factor during a predetermined window time. For example, the factor may include a duration of interference, an amount of power of an interference signal, a last point in time at which the interference occurs before the predetermined point in time, and the like. For example, a ranking of the first frequency 401 may be calculated over time as indicated by a bold arrow indicator 450. A corresponding ranking may frequently vary over time. A ranking of the second frequency 403 may also be calculated as indicated by another bold arrow indicator 460.

Calculation of a ranking is further described with reference to FIGS. 5A and 5B.

Figure 5A:
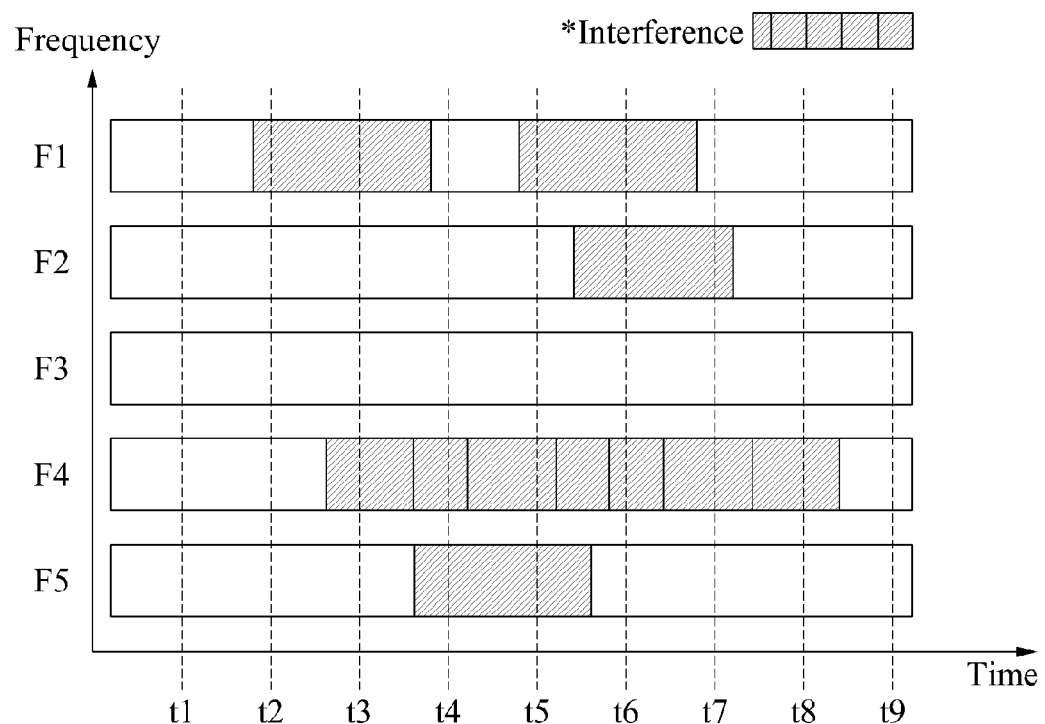

FIG. 5A and FIG. 5B illustrate examples of a wireless communication apparatus between medical devices using cognitive technology to determine a priority of an available frequency.

In this example, a priority may correspond to a ranking.

Referring to FIG. 5A, a graph shows interference that occurs in each of frequencies F1, F2, F3, F4, and F5, based on a time. A variety of interference may occur at each of points in times t1, t2, t3, t4, t5, t6, t7, t8, and t9 with respect to each of the frequencies F1, F2, F3, F4, and F5. The frequencies F1, F2, F3, F4, and F5 may be used for the medical use. At each of the points in times t1 through t9, the frequencies F1, F2, F3, F4, and F5 may be used for a different use other than a medical use, for example, and may be used by a heterogeneous protocol that causes interference to occur. In addition, even if the frequencies are for the medical use, the frequencies F1, F2, F3, F4, and F5 may be used by another device and interference may occur.

FIG. 5B illustrates a result of rankings calculated at the points in times t1 through t9 with respect to the frequencies F1, F2, F3, F4, and F5. The ranking may be calculated according to the following equation.

$$\text{If\_level}(t,f,\text{win}) = k1 \times (\text{duration}) + k2 \times (\text{power}) + k3 \times (1-\text{since})$$

The above equation may express a duration of interference during an amount of window time 'win' at a point in time 't' with respect to a frequency 'f', an amount of power of an interference signal, and a last point in time (1−since) at which the interference occurs before the predetermined point in time t. Each of k1, k2, and k3 corresponds to a weight. The weight may be determined based on an environment of a predetermined area of a ranking. In the example shown in FIG. 5B, k1=10, k2=2, and k3=1.

Referring to the graph of FIG. 5A, interference does not occur at any of the frequencies F1, F2, F3, F4, and F5 at the point in time t1. Accordingly, the wireless communication apparatus may assign all of the frequencies F1, F2, F3, F4, and F5 to the mobile hub.

At the point in time t2, interference occurs in the frequency F1, and thus, the remaining frequencies F2, F3, F4, and F5 excluding the frequency F1 may be assigned to the mobile hub. At the point in time t3, interference occurs in the frequencies F1 and F4 and a duration of interference that occurs in the frequency F1 is longer than a duration of interference occurring in the frequency F4. Accordingly, frequency F4 may be ranked higher than the frequency F1. In the aforementioned manner, a ranking of each of the frequencies F1, F2, F3, F4, and F5 may be predicted at each of the points in times t1 through t9.

An alternative frequency may be determined as a frequency having a highest ranking from among available frequencies at each point in time. In this example, a frequency in which a heterogeneous protocol is sensed may not be included in the available frequency bands.

Figure 6:
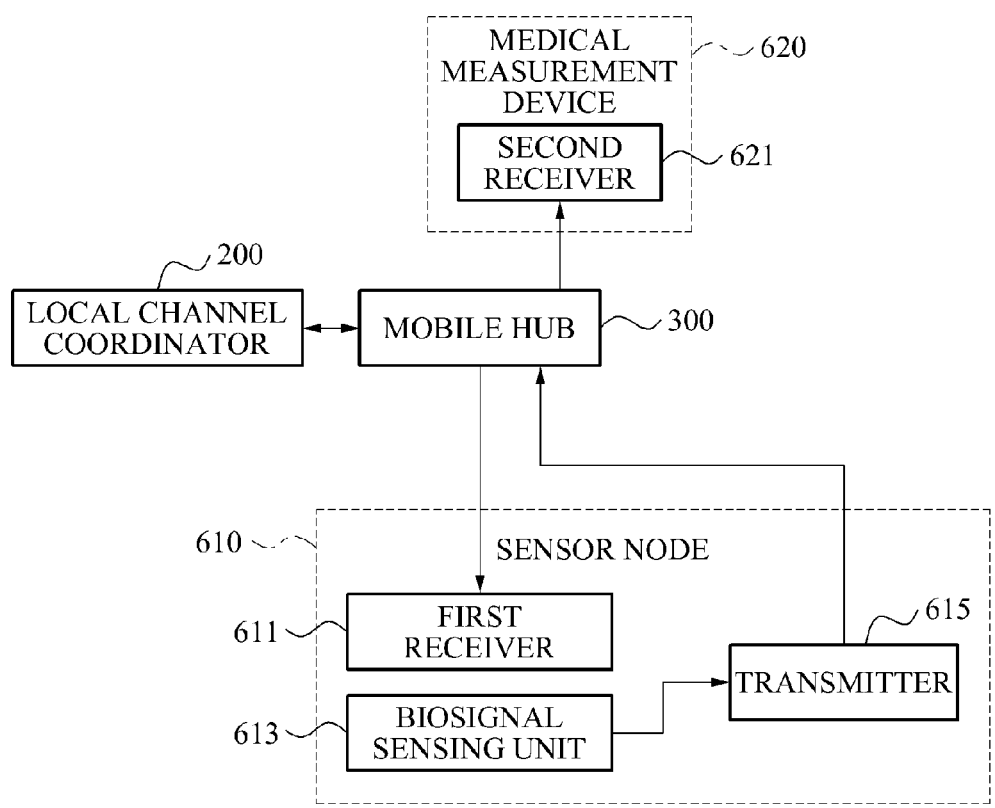
FIG. 6 is a diagram illustrating an example of a wireless communication network system between medical devices using a cognitive technology.

FIG. 6 illustrates an example of a wireless communication network system between medical devices using a cognitive technology.

Referring to FIG. 6, the wireless communication network system includes a local channel coordinator 200, a mobile hub 300, a sensor node 610, and a medical measurement device 620. The local channel coordinator 200 may correspond to the wireless communication apparatus 200 of FIG. 2, and the mobile hub 300 may correspond to the wireless communication apparatus 300 of FIG. 3.

The local channel coordinator 200 may receive state information of frequencies available for a medical use from an external frequency coordination database server. The local channel coordinator 200 may sense an internal interference signal and an external interference signal. For example, the local channel coordinator 200 may receive the internal interference signal from the mobile hub 300.

The local channel coordinator 200 may determine a priority of each frequency that is available in a predetermined area based on the state information, the external interference signal, and the internal interference signal.

The local channel coordinator 200 may assign frequencies to the mobile hub 300 based on the determined priority.

The mobile hub 300 may sense the internal interference signal. In this example, the mobile hub 300 may transmit the internal interference signal to the local channel coordinator 200. The mobile hub 300 may receive the assigned frequencies from the local channel coordinator, and may reassign the assigned frequencies to a wireless node. The wireless node may correspond to a sensor node 610 or a medical measurement device 620. In this example, at least one sensor node or at least one medical measurement device may be provided.

The mobile hub 300 may assign a frequency that has a relatively high priority from among the assigned frequencies to the sensor node 610 over the medical measurement device 620. The sensor node 610 may be attached to a human body to sense a biosignal, and thus, a stable frequency band may need to be assigned to the sensor node 610. Accordingly, the mobile hub 300 may reassign an assigned frequency that has a relatively high priority to the sensor node 610.

A plurality of wireless nodes may be present. The wireless node may communicate with the mobile hub 300 based on the reassigned frequencies. As an example, a communication scheme may include an LDR low power communication scheme.

Referring to the example of FIG. 6, the sensor node 610 includes a first receiver 611, a biosignal sensing unit 613, and a transmitter 615. The first receiver 611 may receive a first frequency that is reassigned from the mobile hub 300. The biosignal sensing unit 613 may sense the biosignal. The transmitter 615 may transmit the sensed biosignal to the mobile hub 300 using the first frequency.

In the example of FIG. 6, the medical measurement device 620 includes a second receiver 621. The second receiver 621 may receive the biosignal and a second frequency that is reassigned from the mobile hub 300. The biosignal may be sensed at the biosignal sensing unit 613.

Referring to FIG. 6, the local channel coordinator 200 may determine a priority of each available frequency such that the sensor node 610 and the medical measurement device 620 may stably perform communication. The local channel coordinator 200 may assign a frequency based on a QoS of the sensor node 610 and the medical measurement device 620 from among frequencies of which priorities are determined. The assigned frequencies that are transferred to the local channel coordinator 200 may be reassigned to the sensor node 610 and the medical measurement device 620 via the mobile hub 300.

In various examples, the wireless communication network system may assign, to the sensor node 610 and the medical measurement device 620, frequencies receiving relatively small interference from among the frequencies that are available for the medical use through the hierarchical structure of the local channel coordinator 200, the mobile hub 300, the sensor node 610, and the medical measurement device 620.

Figure 7:
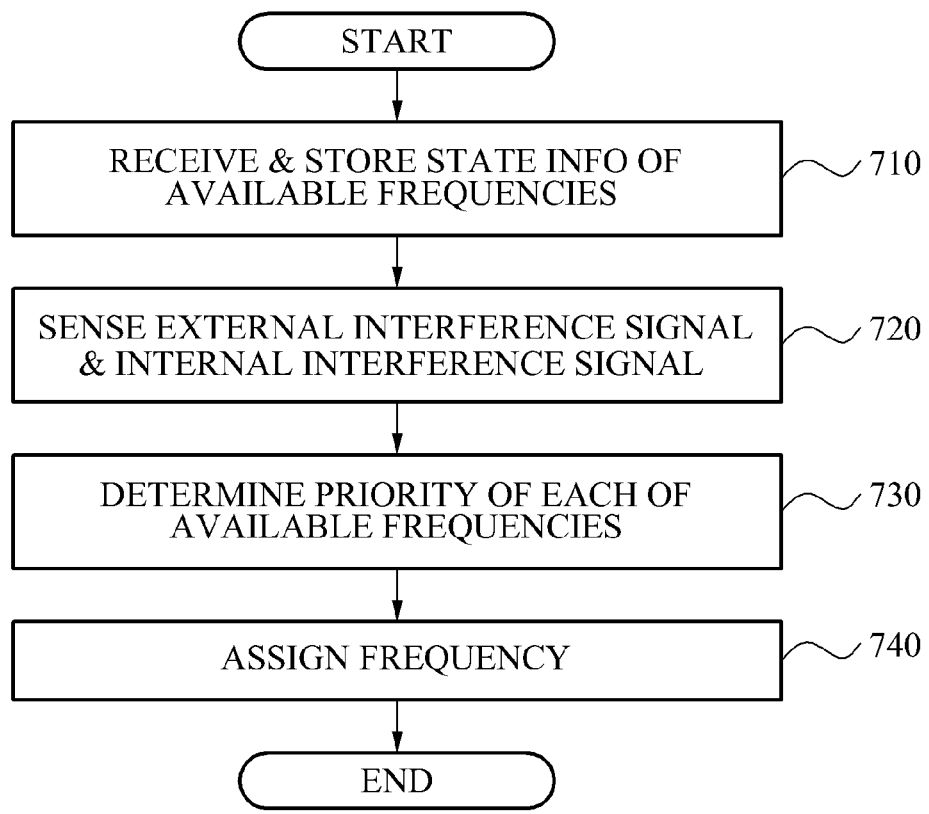
FIG. 7 is a flowchart illustrating an example of a wireless communication method between medical devices using a cognitive technology.

FIG. 7 illustrates an example of a wireless communication method between medical devices using a cognitive technology.

In 710, a wireless communication apparatus between medical devices using the cognitive technology receives state information of frequencies that are available in a predetermined area, and stores interference information associated with the available frequencies. For example, the wireless communication apparatus may receive the state information from an external frequency coordination database server.

In 720, the wireless communication apparatus senses an external interference signal and an internal interference signal. For example, the external interference signal may correspond to an interference signal that affects the available frequencies outside the predetermined area, and the internal interference signal may correspond to an interference signal that affects the available frequencies within the predetermined area.

The wireless communication apparatus may receive the internal interference signal and positioning information of a wireless node that is positioned within the predetermined area, from a mobile hub.

In 730, the wireless communication apparatus determines a priority of each of the frequencies that are available in the predetermined area based on the interference information, the external interference signal, and the internal interference signal. For example, the wireless communication apparatus may determine the priority of each of the frequencies that are available in the predetermined area based on an amount of interference that is measured during a predetermined amount of time.

In 740, the wireless communication apparatus assigns a frequency to the mobile hub based on the priority. In various examples, the wireless communication apparatus may sense interference of a heterogeneous protocol that affects a frequency assigned to a mobile hub, and assign an alternative frequency to the mobile hub in response to the interference of the heterogeneous protocol being sensed.

Figure 8:
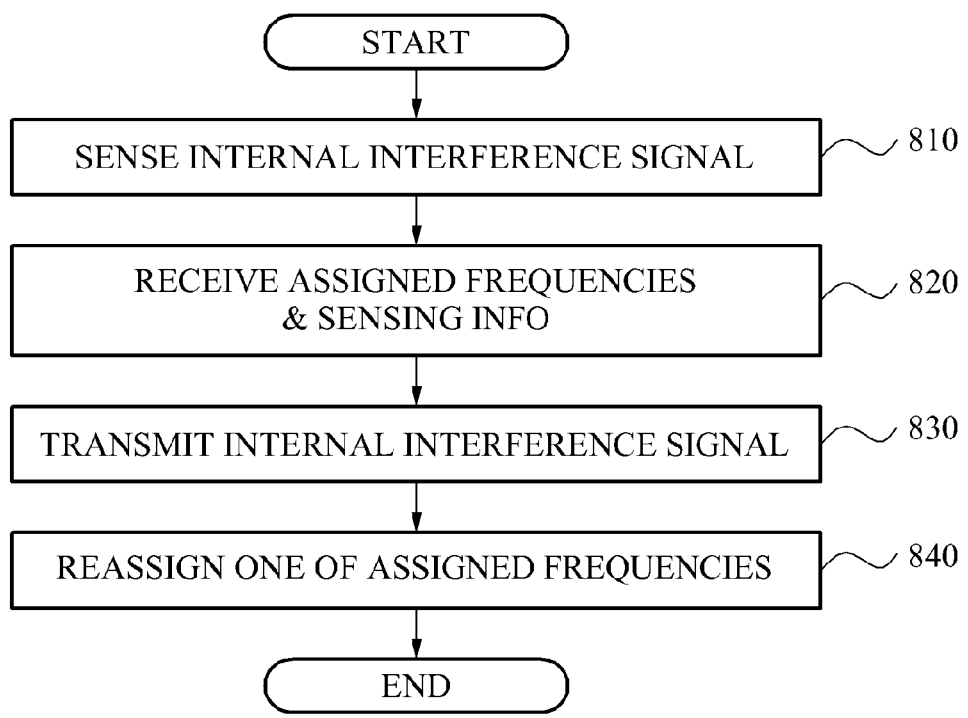
FIG. 8 is a flowchart illustrating another example of a wireless communication method between medical devices using a cognitive technology.

FIG. 8 illustrates another example of a wireless communication method between medical devices using a cognitive technology.

In 810, a wireless communication apparatus between medical devices using the cognitive technology senses an internal interference signal that affects frequencies that are available in a predetermined area. For example, an area within the predetermined area may correspond to a sensing coverage of a mobile hub.

The wireless communication apparatus may sense the internal interference signal that affects frequencies that are assigned from a local channel coordinator, and may sense position information of the mobile hub and position information of at least one sensor node.

The wireless communication apparatus may sense interference of a heterogeneous protocol that affects the assigned frequencies, and may request the local channel coordinator for an alternative frequency in response to the interference of the heterogeneous protocol being sensed.

In 820, the wireless communication apparatus may receives assigned frequencies from the local channel coordinator, and receives sensing information from the at least one sensor node.

In 830, the wireless communication apparatus transmits the internal interference signal to the local channel coordinator.

The wireless communication apparatus may transmit the internal interference signal that affects the assigned frequencies and the position information. The position information may include position information of the mobile hub and position information of the at least one sensor node.

In 840, the wireless communication apparatus reassigns one of the assigned frequencies to the at least one sensor node based on the internal interference signal. For example, the wireless communication apparatus may reassign, to the wireless nodes, frequencies that have a relatively high priority from among the assigned frequencies as the QoS of each of the wireless nodes that have a higher ranking.

Figure 9:
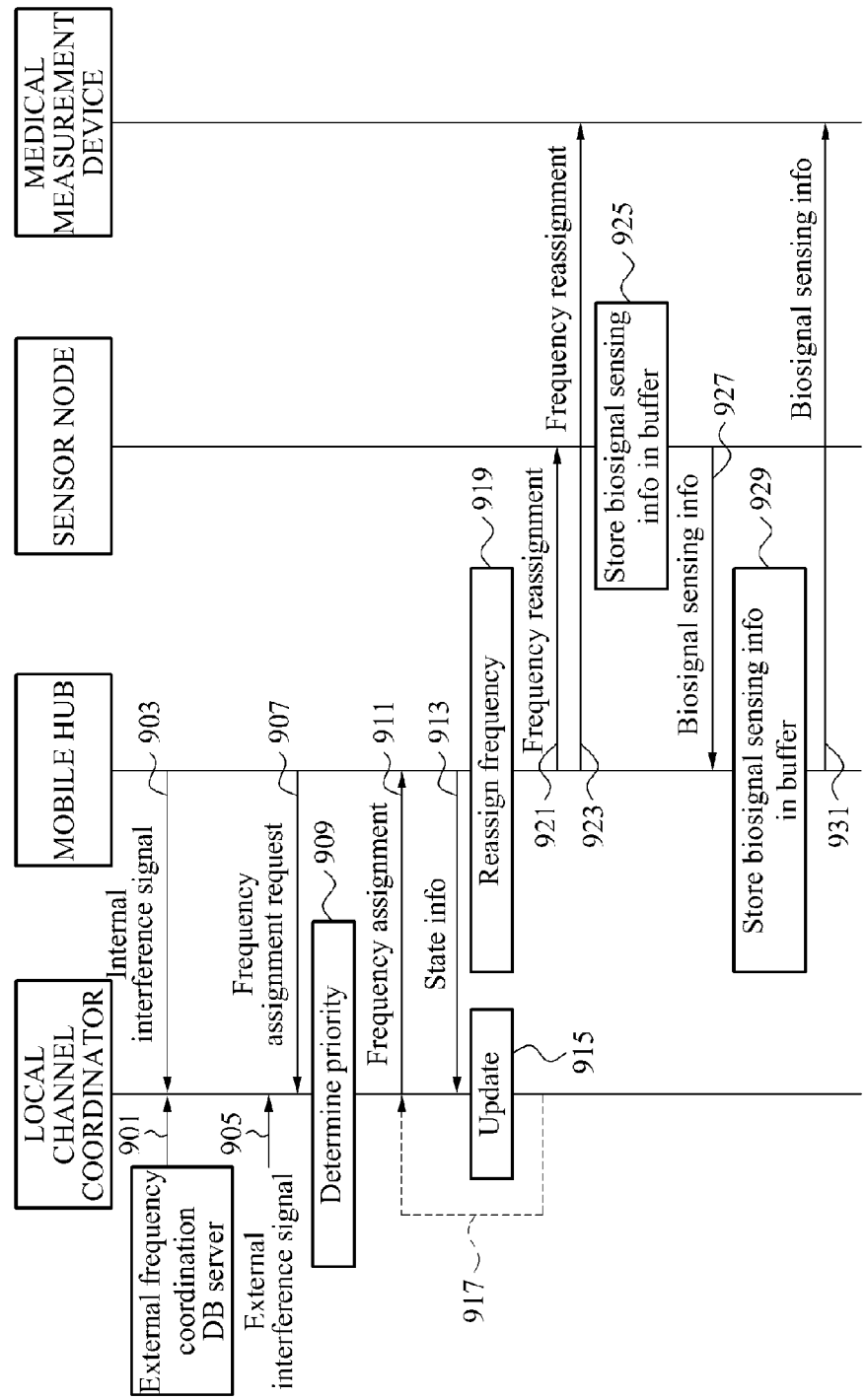
FIG. 9 is a diagram illustrating an example of an operation of entities included in a wireless communication network system between medical devices using a cognitive technology.

FIG. 9 illustrates an example of an operation of entities included in a wireless communication network system between medical devices using a cognitive technology.

Referring to FIG. 9, the wireless communication network system includes a local channel coordinator, a mobile hub, a sensor node, and a medical measurement device.

At 901, the local channel coordinator obtains, from an external frequency coordination database server, state information that is associated with frequencies that are being used from among frequencies that are available for a medical use.

At 903, the mobile hub senses an internal interference signal that affects the available frequencies within a predetermined area, within a sensing coverage, and transmits the internal interference signal to the local channel coordinator.

At 905, the local channel coordinator senses an external interference signal that affects the available frequencies that are outside the predetermined area.

At 907, the mobile hub requests the local channel coordinator for assignment of a frequency for communication to be performed by the sensor node and the medical measurement device.

At 909, the local channel coordinator determines a priority of each of the available frequencies based on the state information, the external interference signal, and the internal interference signal.

At 911, the local channel coordinator assigns, to the mobile hub, frequencies receiving relatively small or minimum amount of interference from among the available frequencies.

At 913, the mobile hub transmits state information that is associated with the assigned frequencies. For example, the state information may include information about whether the assigned frequencies are used by another device, and the internal interference signal.

At 915, the local channel coordinator updates a priority of each of the available frequencies based on the state information. Through the update, frequencies may be stably assigned to the sensor node and the medical measurement device.

At 917, the local channel coordinator reassigns a frequency to the mobile hub.

At 919, the mobile hub reassigns, to the sensor node and the medical measurement device, the frequencies that are assigned from the local channel coordinator based on the QoS. The mobile hub may reassign, to the sensor node, frequencies that have relatively high priorities.

At 921, the mobile hub reassigns, to the sensor node, a frequency that has a relatively high priority.

At 923, the mobile hub reassigns, to the medical measurement device, a frequency that has a relatively low priority in comparison to the priority of the frequency reassigned to the sensor node.

At 925, the sensor node stores biosignal sensing information in a buffer, and prepares to transmit the biosignal sensing information to the mobile hub.

At 927, the sensor node transmits the stored biosignal sensing information to the mobile hub.

At 929, the mobile hub stores the received biosignal sensing information in the buffer. Even though an alternative frequency is assigned due to interference of the heterogeneous protocol, the mobile hub may store the biosignal sensing information in the buffer to stably transfer the biosignal sensing information to the medical measurement device and a wideband communication apparatus.

At 931, the mobile hub transfers the biosignal sensing information to the medical measurement device. In this example, the medical measurement device may analyze the biosignal sensing information, determine an emergency, and generate a corresponding signal.

According to embodiments, there may be provided a method and apparatus that enables stable communication with a sensor node attached to a human body for a medical use, and may manage a communication frequency band by hierarchically employing cognitive technology.

According to embodiments, human body sensor nodes using an ultra low power may stably perform communication by hierarchically employing cognitive technology.

According to embodiment, since cognitive technology is hierarchically employed, stable operation is enabled in a state where external interference occurring between wireless medical devices in a predetermined medical facility is less than an allowance value.

According to embodiments, since an alternative frequency may be set by determining a priority of an available frequency band, stable communication may be performed using the alternative frequency when external interference occurs in a frequency currently used by a wireless medical device.

According to embodiments, it is possible to decrease an amount of power consumed for performing communication between a sensor node and a medical device by hierarchically employing cognitive technology.

The processes, functions, methods and/or software described above may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable storage media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations and methods described above, or vice versa. In addition, a non computer-readable storage medium may be distributed among computer systems connected through a network and non-transitory computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wireless communication apparatus between medical devices using a cognitive technology, the apparatus comprising:
   a frequency database management unit configured to receive, from an external frequency coordination database server, state information of frequencies that are available in a predetermined area, and to store interference information that is associated with the frequencies;
   an interference signal sensing unit configured to sense an external interference signal that affects the frequencies outside the predetermined area, and an internal interference signal that affects the frequencies within the predetermined area; and
   a control unit configured to determine a priority of each of the frequencies that are available in the predetermined area based on the interference information, the external interference signal, and the internal interference signal, and to determine a frequency to be assigned based on the priority.

2. The apparatus of claim 1, wherein the external frequency coordination database server is configured to store information about whether the frequencies are used by a predetermined device that is outside and within the predetermined area.

3. The apparatus of claim 1, wherein the interference signal sensing unit comprises:
   an external interference signal sensing unit configured to sense the external interference signal; and
   an internal interference signal receiver configured to receive, from a mobile hub, the internal interference signal and positioning information of a wireless node that is positioned within the predetermined area.

4. The apparatus of claim 1, wherein the control unit is further configured to determine the priority of each of the frequencies that are available in the predetermined area based on an amount of interference that is measured during a predetermined amount of time.

5. The apparatus of claim 1, wherein the control unit is further configured to determine the priority of each of the frequencies that are available in the predetermined area based on a duration of interference that affects each of the frequencies at a predetermined point in time with respect to each of the frequencies, an amount of power of the interference, and a last point in time at which the interference occurs before the predetermined point in time.

6. The apparatus of claim 1, wherein the control unit is further configured to determine the frequency to be assigned based on a quality of service (QoS) of a wireless node.

7. The apparatus of claim 1, wherein:
the interference signal sensing unit is further configured to sense interference of a heterogeneous protocol that affects a frequency assigned to a mobile hub, and
the control unit is further configured to assign an alternative frequency to the mobile hub in response to the interference of the heterogeneous protocol being sensed.

8. A wireless communication apparatus between medical devices using a cognitive technology, the apparatus comprising:
an interference signal sensing unit configured to sense an internal interference signal that affects frequencies that are available in a predetermined area;
a receiver configured to receive assigned frequencies from a local channel coordinator, and to receive sensing information from at least one sensor node;
a transmitter configured to transmit the sensed internal interference signal to the local channel coordinator; and
a control unit configured to determine a frequency to be reassigned to the at least one sensor node among the assigned frequencies based on the internal interference signal.

9. The apparatus of claim 8, wherein the interference signal sensing unit is further configured to sense an internal interference signal that affects the assigned frequencies, and to sense position information of a mobile hub and position information of at least one sensor node.

10. The apparatus of claim 9, wherein the transmitter is further configured to transmit the internal interference signal that affects the assigned frequencies, the position information of the mobile hub, and the position information of the at least one sensor node.

11. The apparatus of claim 8, wherein the control unit is further configured to determine frequencies to be reassigned to wireless nodes from among the assigned frequencies based on a QoS of each of the wireless nodes, and the wireless nodes comprise the at least one sensor node and a medical measurement device.

12. The apparatus of claim 11, wherein the control unit is further configured to reassign, to the wireless nodes, frequencies that have relatively high priorities from among the assigned frequencies to wireless nodes that have a higher QoS ranking.

13. The apparatus of claim 8, wherein:
the interference signal sensing unit is further configured to sense interference of a heterogeneous protocol that affects the assigned frequencies, and
the control unit is further configured to generate a signal for requesting the local channel coordinator for an alternative frequency in response to the interference of the heterogeneous protocol being sensed.

14. The apparatus of claim 13, wherein the transmitter is further configured to transmit, to the local channel coordinator, a signal for requesting assignment of a frequency and the signal for requesting the alternative frequency.

15. The apparatus of claim 8, further comprising:
a buffer configured to store sensing information from the at least one sensor node.

16. A wireless communication network system between medical devices using a cognitive technology, the system comprising:
a local channel coordinator configured to determine a priority of each of the frequencies that are available in a predetermined area based on state information of frequencies that is received from an external frequency coordination database server, an external interference signal, and an internal interference signal, and to assign frequencies based on the priority;
a mobile hub configured to sense the internal interference signal, to transmit the internal interference signal, to receive the assigned frequencies, and to reassign the assigned frequencies to a plurality of wireless nodes, wherein
the plurality of wireless nodes are configured to perform communication based on the reassigned frequencies.

17. The system of claim 16, wherein:
the plurality of wireless nodes comprise at least one sensor node and at least one medical measurement device;
the at least one sensor node comprises:
a first receiver configured to receive a first frequency that is reassigned from the mobile hub;
a biosignal sensing unit configured to sense a biosignal; and
a transmitter configured to transmit the biosignal to the mobile hub; and
the at least one medical measurement device comprises:
a second receiver configured to receive a second frequency that is reassigned from the mobile hub and the biosignal.

18. The system of claim 17, wherein the mobile hub is further configured to assign a frequency that has a relatively high priority from among the assigned frequencies to the at least one sensor node in a preference over the at least one medical measurement device.

19. A wireless communication method between medical devices using a cognitive technology, the method comprising:
receiving, from an external frequency coordination database server, state information of frequencies that are available in a predetermined area, and storing interference information associated with the frequencies;
sensing an external interference signal that affects the frequencies outside the predetermined area, and an internal interference signal that affects the frequencies within the predetermined area;
determining a priority of each of the frequencies that are available in the predetermined area based on the interference information, the external interference signal, and the internal interference signal; and
assigning a frequency based on the priority.

20. The method of claim 19, wherein the sensing comprises receiving, from a mobile hub, the internal interference signal and positioning information of a wireless node that is positioned within the predetermined area.

21. The method of claim 19, wherein the determining of the priority comprises determining the priority of each of the frequencies that are available in the predetermined area based on an amount of interference that is measured during a predetermined amount of time.

22. The method of claim 19, wherein:
the sensing comprises sensing interference of a heterogeneous protocol that affects a frequency assigned to a mobile hub, and
the assigning comprises assigning an alternative frequency to the mobile hub in response to the interference of the heterogeneous protocol being sensed.

23. A wireless communication method between medical devices using a cognitive technology, the method comprising:

sensing an internal interference signal that affects frequencies that are available in a predetermined area;
receiving assigned frequencies from a local channel coordinator, and receiving sensing information from at least one sensor node;
transmitting the sensed internal interference signal to the local channel coordinator; and
reassigning one of the assigned frequencies to the at least one sensor node based on the internal interference signal.

24. The method of claim 23, wherein the sensing comprises sensing an internal interference signal that affects the assigned frequencies, and sensing position information of a mobile hub and position information of at least one sensor node.

25. The method of claim 24, wherein the transmitting comprises transmitting the internal interference signal that affects the assigned frequencies, the position information of the mobile hub, and the position information of the at least one sensor node.

26. The method of claim 23, wherein the reassigning comprises reassigning, to the wireless nodes, frequencies that have relatively high priorities from among the assigned frequencies to wireless nodes that have a higher QoS ranking.

27. The method of claim 23, wherein the sensing comprises sensing interference of a heterogeneous protocol that affects the assigned frequencies, and requesting the local channel coordinator for an alternative frequency in response to the interference of the heterogeneous protocol being sensed.

* * * * *